(12) United States Patent
Fleischner

(10) Patent No.: US 6,841,176 B2
(45) Date of Patent: Jan. 11, 2005

(54) IMMUNITY ENHANCING SUPPLEMENTS FOR LUNG SUPPORT

(75) Inventor: Albert M Fleischner, Westwood, NJ (US)

(73) Assignee: Goen Technologies, Inc., Cedar Knolls, NJ (US)

( * ) Notice: Subject to any disclaimer, the term of this patent is extended or adjusted under 35 U.S.C. 154(b) by 321 days.

(21) Appl. No.: 10/191,272

(22) Filed: Jul. 9, 2002

(65) Prior Publication Data

US 2003/0072823 A1 Apr. 17, 2003

Related U.S. Application Data

(63) Continuation-in-part of application No. 09/842,428, filed on Apr. 27, 2001, now abandoned.

(51) Int. Cl.$^7$ .............................................. A61K 35/78
(52) U.S. Cl. ...................... 424/729; 424/725; 424/743; 424/756; 424/757; 424/773; 424/775
(58) Field of Search ................................ 424/725, 729, 424/743, 756, 757, 773, 775

(56) References Cited

PUBLICATIONS

Calvin A. Lang et al., "Blood Glutathione Decreases in Chronic Diseases," 135 J.Lab.Clin.Med.402 (2000).
Calvin A. Lang et al., "Low Blood Glutathione Levels in Healthy Aging Adults," —J.Lab.Clin.Med. 720 (Nov. 1992).
Steven J. Milloy, "Antioxidant Protect Lungs," http://junkscience.com/news2/antiox.htm(Apr. 18, 1998).
Guizhou Hu et al., "Antioxidants and Pulmonary Function," 151 Am. J. Epidemiol. 975 (2000) (abstract only).
For My Health Dot Com, "N–Acetyl–Cysteine," http://formyhealth.com/nac_article.htm ( Mar. 30, 1999).
C.F.M.R., "N–Acetyl–L–Cysteine," http://www.cochranfoundation.com/reports/nac.htm (Oct. 25, 2000).
"Glutathione and the Elderly," 47(9) J.Clin.Epidemiol. 1021 (1994) (abstract only).
Srah Goodwin et al., "Oral Exposure to Anti–Oxidant Glutathione Could Help Prevent Flu Infections," www.emory.edu/WHSC/ (Apr. 17, 2000).
Holly Korschun, "Jones Discovers New Wepon Against Flu," 52 Emory Report (May 8, 2000).
HealthWell.Com, "Bronchitis," http://www.healthwell.com/healthnotes/concern/bronchitis.ctm (Aug. 2, 1999).
Ron Kennedy, "N–Acetyl–Cysteine," http://www.medical-library.net/sites/_n–acetyl–1–cysteine_(nac).html (Oct. 25, 2000).
S.C. De Rosa et al., "N–Acetylcysteine Replenishes Glutathione In HIV Infection," 1 Eur.J.Clin.Invest. (Oct. 30, 2000) (abstract only).
N. Van Zandwijk, "N–Acetylcysteine for Lung Cancer Prevention," 107 Chest 1437 (1995) (abstract only).
M.P.K.J. Engelen et al., "Altered Glutamate Metabolism Is Associated With Reduced Muscle Glutathione Levels . . . ," 161 Am..Respir.Care Med. 98 (2000).
"Why Do We Need Vitamin A?," http://www.goaskalice.columbia.edu/1132.htm (Nov. 7, 2000).
James F. Balch, Prescription for Nutritional Healing . . . , pp. 13, 14, 16, 65, 77 (1997).
John S. James, "Licorice, Glycyrrhizin and AIDS/ARC," http://www.aids.org/immunet/ath.hst/page/a–017–01 (Nov. 7, 1986).
"Chamomile," http://www/hannet.faithweb.com/chamomile.html (Nov. 8, 2000).
G.E. Trease et al., Pharmacognosy pp. 367, 485, 77, 65 (12th ed.) 1983.
A. Leung et al., "Gotu Kola," 2 Encyclopedia of Common Natural Ingredients Used In Food, Drugs and Cosmetics, 284 (1996).
K. Polasa et al., "Effect of Turmeric On Urinary Mutagens In Smokers," 7 Mutagenesis 107 (1992) (abstract only).
"Turmeric Root," http://onhealth.webmd.com/alternative/resource/herbs/item,16064.asp (Jan. 18, 2001).

Primary Examiner—Herbert J. Lilling
(74) Attorney, Agent, or Firm—Pharmaceutical Patent Attorneys, LLC

(57) ABSTRACT

Supplement compositions designed to support healthy lung function and to help strengthen the immune system.

2 Claims, No Drawings

IMMUNITY ENHANCING SUPPLEMENTS FOR LUNG SUPPORT

This application is a continuation-in-part of Ser. No. 09/842,428 filed Apr. 27, 2001, now abandoned.

BACKGROUND

The prior art regarding this invention arises from distinct areas not heretofore combined to create new and useful formula sets or new and useful improvements thereof regarding Immunity Enhancing Supplements for Lung Support.

This invention relates to the evolving science that several lung disorders are believed to be characterized by low glutathione levels. Glutathione is involved in numerous vital processes. Low glutathione levels have been implicated in inflammatory lung disorders and have been linked to abnormalities in the lung surfactant system and can cause abnormalities in the epithelial lining fluid. Reduced glutathione levels are a risk factor for chronic diseases[1]. Glutathione levels reduce naturally as we age; elderly people may then be at risk because of a decreased capacity to maintain many metabolic and detoxification reactions mediated by glutathione[2]. The key ingredient in this invention, N-Acetyl Cysteine, increases intercellular glutathione and has been shown to reduce the number of infectious bacteria in chronic bronchitis caused by smoking. N-Acetyl Cysteine is a better source of glutathione than taking glutathione itself because less than half of supplemental glutathione gets out of the digestive system and into the body. In addition, N-Acetyl Cysteine is a powerful antioxidant, antitoxin and immune support substance.

Albert M. Fleischner, Ph.D., has a doctorate in Pharmaceutical Chemistry from Rutgers University and has had over thirty years experience in the pharmaceutical industry with firms such as Schering-Plough Corporation, Roberts Pharmaceutical Corporation, Lehn & Fink Division of Sterling Drugs, Bradley Pharmaceutical Corporation, Amerchol Division of CPC and the Goen Group companies. He has a number of published papers and two previously granted patents and has several patents pending.

Not only do the lungs enable us to breathe, but in doing so they help the body eliminate waste gasses. When air is pulled in through the nose and mouth, it enters the trachea and moves down to the broncus, which divide into left and right bronchial tubes. These tubes carry air into the lungs where it is further divided into alveoli, little air sacs, which hold oxygen. As blood flows into the lungs through the capillaries, it brings with it carbon dioxide and other waste gasses. The carbon dioxide and waste gasses switch places with the oxygen as you breathe and the waste gasses are eliminated as you exhale. The oxygen is then distributed throughout the body.

SUMMARY

The invention discloses the formula sets that embody the invention of the supplement composition for increasing glutathione and antioxidant and antitoxin levels to achieve and maintain a healthy status. According to a Cornell University study, antioxidants seem to help protect lung function and may help prevent asthma, emphysema and chronic bronchitis. Specifically, in terms of lung function as measured by how much air the lungs could expel, the difference between people with above-average levels of all the major antioxidants and those with below-average levels is about equivalent to the difference between the lung function of nonsmokers versus those who've smoked a pack a day for 10 years.[3]

N-Acetyl Cysteine works to maintain glutathione and related antioxidant levels that normally decrease with stress, injury, exercise or age, while enhancing vitamin C's ability to support the immune system. This is particularly important since, as the body ages, the ability to digest and absorb protein is reduced over the years, resulting in shortages that lead to disease. Key groups that become oxidized are smokers, those deficient in antioxidants, those under stress and those who are aging. Oxidization makes us more susceptible to viral infection. Studies at the Louisville School of Medicine clearly show that glutathione possesses a unique ability to slow the aging process.[4]

Glutathione levels in the blood and tissues decrease with age[5]; higher glutathione levels are related to higher levels of physical health.[6] Exposure to glutathione can enhance our antioxidant defenses.[7] In a double-blind study, individuals with chronic bronchitis showed a significant reduction in the number of exacerbations of their illness.[8] Smokers have also benefited from taking N-Acetyl Cysteine[9]. In addition to helping break up mucus, N-Acetyl Cysteine may reduce the elevated bacterial counts that are often seen in the lungs of smokers with chronic bronchitis.[10] In another study, people with chronic bronchitis who took N-Acetyl Cysteine showed an improved ability to expectorate and a reduction in cough severity.[11] These benefits may result from N-Acetyl Cysteine's capacity to reduce the viscosity of sputum.[12]

N-Acetyl Cysteine has been shown to provide protection against free radicals as well as against a variety of toxic hazards such as: acrolein (found in barbecue and cigarette smoke and auto exhaust), bromobenzene, paraquat (a toxic herbicide) and the side effects of cyclophosphamide and adrimycin (anti-cancer drugs).[13] Diseases in which free radicals play a role include cancer, AIDS, cirrhosis and many others. According to a study at Stanford University, patients given N-Acetyl Cysteine daily for six weeks were roughly twice as likely to survive for two years as the subject that did not take N-Acetyl Cysteine.[14]

In reviewing approximately 200 published studies, there was overwhelming evidence that antioxidants are associated with reduced cancer incidence. Antioxidants neutralize free radicals, which are produced by normal metabolic activity. Without antioxidants, free radicals would damage cells and DNA and is a major factor in cancer and aging. Cigarette smoke contains oxidants as well as several precarcinogens. Metabolism of carcinogens and the steps of carcinogenesis are a balance between metabolic activation and detoxification, formation and scavenging of radicals and DNA damage and repair. This suggests that carcinogenic compounds can initiate tumor growth only when they saturate detoxification pathways. Glutathione plays a role in the detoxification of xenobiotics. N-Acetyl Cysteine has been shown to have important chemopreventive properties and may provide protection against different mutagens and carcinogens in different stages of carcinogenesis.[15] A study at Harvard Medical School found that while glutathione aids in the protection of all cells and membranes, it is especially able to enhance immune system cells, protecting against damage from radiation and helping to reduce the side effects of chemotherapy, x-rays and alcohol.

N-Acetyl Cysteine has reached the Phase III trial stage in chemoprevention in Europe and has been used in clinical practice there for more than 30 years. In large groups of patients with chronic obstructive lung disease, N-Acetyl Cysteine has been a safe agent with minor effects even when prescribed for a prolonged period.[16]

N-Acetyl Cysteine is an excellent mucolytic agent. It keeps the membranes of the respiratory system moist, thereby lessening the irritation of dry air, dust and pollutants. It also helps the immune system to do its job properly in the respiratory tract. A study conducted by the Departments of Pulmonology and Surgery at Maastricht University and at the Asthma Centre Homerheide, both in The Netherlands, found that altered glutamate metabolism is associated with reduced muscle glutathione levels in patients with emphysema.[17]

Science already knows that N-Acetyl Cysteine has demonstrated in clinical studies that it can help protect, prevent and repair damaged cells and DNA. This invention takes that information and embodies it in a new and useful set of formulae, disclosed herein.

We now discuss in detail the most preferred version, variants or embodiments of the invention. First, a few words on terminology. The claim term "a" includes one and more than one. The claim term "label" is used as defined in the Federal Food Drug & Cosmetic Act and the regulations promulgated thereunder. We now turn to discussing in great detail the best (or "preferred") versions (or "embodiments") of the invention.

The composition of each unit of the lung support supplement includes any combination of the specified range of the following ingredients:

| | |
|---|---|
| Vitamin A (as retinyl palmitate) | 1,000 IU–10,000 IU |
| Vitamin B<sub>6</sub> (as pyridoxine HCI) | 1 mg–50 mg |
| N-Acetyl-cysteine | 25 mg–500 mg |
| Deglychrrhizinated licorice root extract | 25 mg–200 mg |
| Matricaria chamomile (flowering tops) | 10 mg–150 mg |
| Slippery elm bark | 10 mg–150 mg |
| Sarsaparilla | 25 mg–100 mg |
| Astralagus root | 10 mg–100 mg |
| Gotu kola leaf extract (10% asiaticosides) | 10 mg–50 mg |
| Turmeric rhizome standardized extract (95% curcuminoids) | 5 mg–20 mg |

A representative formula for lung support supplement is as follows, one tablet contains:

| | |
|---|---|
| Vitamin A (as retinyl palmitate) | 1,250 IU |
| Vitamin B$_6$ (as pyridoxine HCI) | 5 mg |
| N-Acetyl-cysteine | 250 mg |
| Deglychrrhizinated licorice root extract | 100 mg |
| Matricaria chamomile (flowering tops) | 75 mg |
| Slippery elm bark | 75 mg |
| Sarsaparilla root | 50 mg |
| Astralagus root | 25 mg |
| Gotu kola leaf extract (10% asiaticosides) | 225 mg |
| Turmeric rhizome standardized extract (95% curcuminoids) | 125 mg |

The scientific rationale for the formulation is as follows:

Vitamin A maintains the cells that line the respiratory tract. It is vital for normal reproduction, growth and development. Vitamin A has also been shown to be crucial to the immune system, ultimately forming an important defense against diseases. It is an antioxidant that is necessary for new cell growth. Vitamin A deficiency has been associated with greater susceptibility to carcinogens and an increased risk of cancer. By strengthening the immune system, it increases resistance to infections, including colds, sore throats, flu, and bronchitis[18].

Vitamin B6, acting as a coenzyme, aids in immune system function and in antibody production. It plays a role in cancer immunity and aids in the prevention of arteriosclerosis[19].

N-Acetyl Cysteine is used for the reasons set forth above.

Deglycyrrhizinated licorice root soothes inflamed mucous membranes (demulcent effect) of the lungs and has expectorant properties[20]. It also has antiviral properties[21&22].

Chamomile is used to soothe respiratory tract inflammation[23]. It has been suggested that there is a stimulation of local prostaglandin synthesis, thus strengthening the protective mucosal barrier against ulceration[24].

The chief constituent of slippery elm bark is mucilage, which has demulcent, emollient and nutritive properties[25].

Sarsaparilla was used as an expectorant and cough remedy as early as 1738 in Europe; it then gained favor in the colonies. While its mode of action is obscure, it may aid in the absorption of other ingredients[26]. Sarsaparilla root protects against free radical harm from radiation exposure[27].

Astragalus root acts as a tonic to protect the immune system[28]. It is traditionally considered to benefit the body's resistance, reduce swelling and regenerate tissue. Modern uses include support for those suffering from the common cold, immune-deficiency related problems (including AIDS, cancer and tumors) and influenza; it is known to strengthen the body's defenses and is effective for chronic lung weakness[29].

Gotu kola leaf extract has been used to bring down a fever and to relieve colds and upper respiratory infections. Gotu kola has anti-inflammatory, anticonvulsant, antidepressant and analgesic properties[30]. Extracts have been found to promote wound healing[31]. This herb aids in the elimination of excess fluids and shrinks tissues[32].

Turmeric has anti-inflammatory and cytotoxic effects[33]. Regular dietary intake of turmeric provides effective antimutagen action and may be useful in chemoprevention[34]. In vitro and in vivo experiments have found that turmeric has antihepatotoxic and antibacterial effects[35]. The protective, antioxidant effects of turmeric and curcumin were greater than those of vitamins E and A[36].

Without further elaboration, it is believed that one skilled in the art can, using the preceding description, utilize the present invention to its fullest extent. The specific formulas are included as a preferred embodiment of the composition formula ranges, and not to further qualify the description. Claim references to specific components include the component itself, as well as concentrates, metabolites, constituents, extracts or combinations of said ingredients.

[1] *J Lab Clin Med* 2000;135:402–5
[2] *J Lab Clin Med* 1992;120:720–5
[3] Hu G, Cassano P. Antioxidant Nutrients and Pulmonary Functions: The Third national Health and Nutrition Examination Survey (NHANES III). *Am J Epidemiol* 2000;151:975–81.
[4] www.formyhealth.com/nac_article.htm.
[5] *J Lab Clin Med* 1992; 720–5.
[6] *Brit J Clin Epid* 1994; 47:1021–6.
[7] Korschun H. Jones Discovers New Weapon Against Flu. *Emory Report* 2000;Vol. 52, 32.
[8] Grassi C, Morandini G C. A controlled trial of intermittent oral acetylcysteine in the long-term treatment of chronic bronchitis. *Eur J Clin Pharmacol* 1976;9:393–96.
[9] Boman G. Backer U, Larrson S, et al. Oral acetylcysteine reduces exacerbation rate in chronic bronchitis: report of a trial organized by the Swedish Society for Pulmonary Diseases. *Eur J Respir Dis* 1983;64:405–15.
[10] Riise G C, Larsson S, Larsson P, et al. The intrabronchial microbial flora in chronic bronchitis patients: a target for N-acetylcysteine therapy? *Eur Respir J* 1994;7:94–101.
[11] Jackson I M, Barnes J, Cooksey P. Efficacy and tolerability of oral acetylcysteine (Fabrol) in chronic bronchitis: a double-blind placebo controlled study. *J Int Med Res* 1984;12:198–206.

[12] Tattersall A B, Bridgman K M, Huitson A. Acetylcysteine (Fabrol) in chronic bronchitis—a study in general practice. *J Int Med Res* 1983;11:279–84.

[13] Kennedy, R, N-Acetyl-L-Cysteine www.medical-library.net/sites/-n-acetyl-1-cysteine (nac).html.

[14] DeRosa S C, Zaretsky M D, Dubs J G, Roederer M. N-acetylcysteine replenishes glutathione in HIV infection. *Eur J Clin Inv* 2000;30:915+929 Paper 736.

[15] Van Zandwijk N. N-Acetylcysteine for Lung Cancer Prevention. *CHEST* 1995; 107(5): 1437–1441.

[16] ibid.

[17] Engelen M, Schols A, Does J., et. al. Altered glutamate metabolism is associated with reduced muscle glutathione levels in patients with emphysema. *Am J Respir Crit Care Med* 2000;1:98–103 Vol. 161, No. 1.

[18] www.goaskalice.columbia.edu/1132.html.

[19] Balch, James F. *Prescription for Nutritional Healing: A Practical A to Z Reference to Drug-Free Remedies Using Vitamins, Minerals, Herbs & Food Supplements*/James F. Balch, Phyllis A. Balch.—2nd ed. 1977. p.16.

[20] Tyler V. E., Brady L. R. *Pharmacognosy*, 8th ed. p. 69.

[21] Pompei, R., Flore, O., Marccialis, M. A., Pani, A., & Loddo, B. Glycyrrhizic acid inhibits virus growth and inactivates virus particles. *Nature* 1979; 281:689–690.

[22] Shinada, M. et al. Enhancement of interferon gamma production in glycyrrhizin-treated human peripheral lymphocytes in response to concanavalin A and to surface antigen of hepatitis B virus. *Proceedings of the Society for Experimental Biology and Medicine* 1986; 181:205–210.

[23] www.nahnet.faithweb.com/chamomile.html.

[24] ibid.

[25] Trease G. E., Evans, W. C. *Pharmacognosy*, 12th ed. p. 367.

[26] ibid, p. 485.

[27] Balch, p. 77.

[28] ibid. p. 65.

[29] ibid.

[30] Leung, A., Foster, S. *Encyclopedia of Common Natural Ingredients Used in Food, Drugs, and Cosmetics.* 1996;2:284.

[31] ibid.

[32] Balch, p. 71.

[33] But, P. P. H. et al. (eds.). 1997. *International Collation of Traditional and Folk Medicine*. Singapore: World Scientific. 207–208.

[34] Polasa, K., T. C. Raghuram, T. P. Krishna, K. Krishnaswamy. 1992. Effect of turmeric on urinary mutagens in smokers. *Mutagenesis* 7(2):107–109.

[35] Kiso, Y., Y. Suzuki, N. Watanabe, Y. Oshima, H. Hikino. 1983. Antihepatotoxic principles of *Curcuma longa* rhizomes. *Planta Med* 49(3):185–187.

[36] Subramanian, M., M. Sreejayan, N. Rao, T. P. Devasagayam, B. B. Singh. 1994. Diminution of singlet oxygen-induced DNA damage by curcumin and related antioxidants. *Mutat Res* 311(2):249–255.

I accordingly disclose here a composition of matter comprising:

N-Acetyl-L-cysteine in an amount effective to maintain healthy serum glutathione levels;

retinyl palmatate in an amount effective as a dietary antioxidant;

pyridoxine hydrochloride in an amount effective to aid in immune system function;

licorice root extract in an amount effective as an expectorant;

chamomile flower in an amount effective to soothe respiratory tract inflammation;

slippery elm bark in an amount effective as a demulcent;

sarsaparilla root in an amount effective as an expectorant;

astragalus root in an amount effective as an immune system protectant;

gotu kola in an amount effective as an anti-inflammatory; and turmeric in an amount effective as an anti-inflammatory.

I similarly disclose a composition of matter intended to support healthy lung function, comprising:

from about 25 mg to about 500 mg of N-Acetyl-L-cysteine;

from about 2.4 mg to about 24 mg of retinyl palmatate;

from about 1.3 mg to about 65 mg of pyridoxine hydrochloride;

from about 10 mg to about 100 mg of licorice root extract;

from about 10 mg to about 150 mg of chamomile flower;

from about 10 mg to about 150 mg of slippery elm bark;

from about 10 mg to about 50 mg of sarsaparilla root;

from about 10 mg to about 100 mg of astragalus root;

from about 10 mg to about 50 mg of gotu kola leaf extract; and from about 5 mg to about 20 mg of turmeric rhizome standardized extract.

I claim:

1. A composition of matter intended to support healthy lung function, said composition of matter comprising:

N-Acetyl-L-cysteine in an amount effective to maintain healthy serum glutathione levels;

retinyl palmate in an amount effective as a dietary antioxidant;

pyridoxine hydrochloride in an amount effective to aid in immune system function;

licorice root extract in an amount effective as an expectorant;

chamomile flower in an amount effective to soothe respiratory tract inflammation;

slippery elm bark in an amount effective as a demulcent;

sarsaparilla root in an amount effective as an expectorant;

astragalus root in an amount effective as an immune system protectant;

gotu kola in an amount effective as an anti-inflammatory; and turmeric in an amount effective as an anti-inflammatory.

2. A composition of matter intended to support healthy lung function, said composition of matter comprising:

from about 25 mg to about 500 mg of N-Acetyl-L-cysteine;

from about 2.4 mg to about 24 mg of retinyl palmate;

from about 1.3 mg to about 65 mg of pyridoxine hydrochloride;

from about 10 mg to about 100 mg of licorice root extract;

from about 10 mg to about 150 mg of chamomile flower;

from about 10 mg to about 150 mg of slippery elm bark;

from about 10 mg to about 50 mg of sarsaparilla root;

from about 10 mg to about 100 mg of astragalus root;

from about 10 mg to about 50 mg of gotu kola leaf extract; and from about 5 mg to about 20 mg of turmeric rhizome standardized extract.

* * * * *